United States Patent [19]

Plumb

[11] Patent Number: 4,863,692
[45] Date of Patent: Sep. 5, 1989

[54] APPARATUS FOR DETECTING OIL AND OTHER LIGHTER-THAN-WATER CONTAMINANTS IN AN EFFLUENT STREAM

[76] Inventor: Arnold D. Plumb, 6918 E. 63rd St., Tulsa, Okla. 74133

[21] Appl. No.: 203,416

[22] Filed: Jun. 7, 1988

[51] Int. Cl.[4] ............................................. G01N 31/22
[52] U.S. Cl. ......................................... 422/58; 436/28; 436/29; 436/60; 436/163; 73/323; 73/863.81; 210/95; 422/69
[58] Field of Search .................... 422/58, 61, 86, 87, 422/88, 69; 436/1, 3, 28, 29, 60, 61, 163; 73/61 R, 61.1 R, 323, 863.71, 863.81, 863.82; 210/93, 94, 95, 671; 166/336, 337

[56] References Cited

U.S. PATENT DOCUMENTS

| | | | |
|---|---|---|---|
| 2,655,893 | 10/1953 | Cox et al. | 210/94 X |
| 3,192,764 | 7/1965 | Jasek | 73/61.1 R |
| 3,400,575 | 9/1968 | Madden | 73/61 R |
| 3,617,551 | 11/1971 | Johnston et al. | 210/671 X |
| 3,764,527 | 10/1973 | Sohl | 210/671 |
| 3,845,661 | 11/1974 | Hollweck et al. | 374/208 |
| 3,887,907 | 6/1975 | Brill | 73/61.1 R |
| 3,924,449 | 12/1975 | Moreau et al. | 73/61.1 R |
| 3,929,003 | 12/1975 | Llewellyn | 73/61.1 R |
| 3,985,020 | 10/1976 | Moreau | 73/61.1 R |
| 4,131,773 | 12/1978 | Maham et al. | 200/61.05 |
| 4,223,552 | 9/1980 | Goldstein | 73/61.1 R |
| 4,287,763 | 9/1978 | Richard | 73/863.21 |
| 4,303,408 | 12/1981 | Kim et al. | 436/175 |
| 4,363,639 | 12/1982 | Gladon | 55/95 |
| 4,511,461 | 4/1985 | Kruyer | 209/47 |
| 4,658,861 | 4/1987 | Roberson, Sr. | 138/90 |

*Primary Examiner*—Michael S. Marcus
*Assistant Examiner*—Rebekah A. Griffith
*Attorney, Agent, or Firm*—Hewitt, Kimball & Krieger Pravel, Gambrell

[57] ABSTRACT

An apparatus for detecting oil and other lighter-than-water contaminants in an effluent stream in a sewage system. The apparatus includes a disposable detector which floats in the effluent stream and detects oil and other contaminants having a specific gravity lighter than the water by absorbing the oil and such contaminants in an oleophilic material, permitting the oil and other contaminants to rise and collect in a collection tube. The acidity or pH of the effluent being monitored is determined by routing a portion of the effluent stream through the lower side of the detector across a litmus paper. The detector is held in the sewage system by a securing system which indicates whether the detector has been tampered with since it was installed.

17 Claims, 2 Drawing Sheets

APPARATUS FOR DETECTING OIL AND OTHER LIGHTER-THAN-WATER CONTAMINANTS IN AN EFFLUENT STREAM

BACKGROUND OF THE INVENTION

1. Field of the Invention

This invention relates to an apparatus for detecting oil and other lighter-than-water contaminants in an effluent stream, and in one of its aspects, this invention relates to an apparatus for continuously detecting the presence of oil and other lighter-than-water contaminants and the acidity or pH of an effluent stream which includes a system for securing the detector within the pipeline to determine if the detector has been tampered with.

2. Description of the Prior Art

Environmental regulations have been promulgated which require that the effluent stream of commercial establishments be monitored to determine if any oil is being discharged and to measure the pH of the waste water.

Consequently, there is a need for an inexpensive and disposable detector which can be inserted into the sewage system of a commercial establishment using the conventional access line. Further, there is a need for such a detector which can be secured to the access line to determine if anyone has tampered with the detector since it was installed. While there are apparatus for detecting the presence of oil in a body of water, see for example U.S. Pat. Nos. 4,131,773 and 4,223,552, and for extracting a sample from a stream at a specified time, see for example U.S. Pat. No. 3,400,575, there is a need for a device which can be installed directly into a sewage system to continuously sample the effluent stream. Further, there is a need for such a device to indicate if the detector portion has been removed or otherwise tampered with.

SUMMARY OF THE INVENTION

Briefly, the invention relates to an apparatus for detecting oil and other lighter-than-water contaminants in an effluent stream. The detector, which is secured within the pipeline, includes a housing having an inlet and an outlet. Supported within the housing is an oleophilic material through which at least a portion of the effluent stream passes. Oil and other contaminants having a specific gravity lighter than water are absorbed by the oleophilic material and migrate upwardly to the top of the oleophilic material. At that point, the oil is routed through a channel into a collection tube for visual observation when the detector is removed. A portion of the effluent stream passes through a second channel where the pH of the effluent stream is measured.

To confirm the accuracy of the data obtained and ensure that no one has tampered with the detector since it was installed, the present invention includes a cap which is attached to the access line of the sewage system. The cap includes a recessed portion which is adapted to engage a plug having about the same outer width dimension as the recessed portion. One end of the plug includes a connector which attaches to a lead line of the detector. The detector is connected to the plug and the plug inserted into the recessed portion of the cap. The cap is attached to the access line of the sewage system. A cover plate is installed over the cap and secured in place. Security tape and other security-type locks well known to those skilled in the art are then inserted or installed across the access line and the cap. In this manner, an inspector may visually observe whether the cap has been tampered with since the detector was installed.

Examples of the more important features of this invention have been summarized rather broadly in order that the detailed description may be better understood. There are, of course, additional features of the invention which will be described hereafter and which will also form the subject of the claims appended hereto.

BRIEF DESCRIPTION OF THE DRAWINGS

In order to more fully understand the drawings used and the detail description of the present invention, a brief description of each drawing is provided.

DETAILED DESCRIPTION OF THE PREFERRED EMBODIMENT

Figure 1:
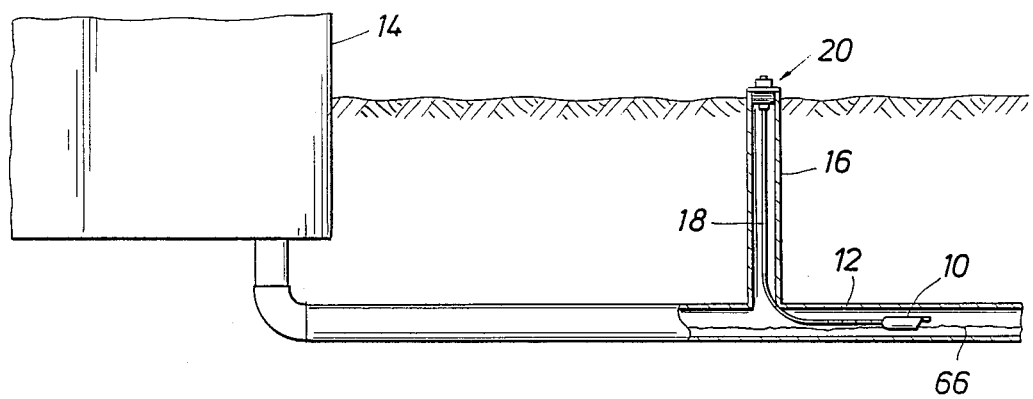
FIG. 1 is a cross-sectional elevation view illustrating the present invention installed in a sewage system.

Referring to FIG. 1, a detector 10 is secured within the sewage system 12 of a building structure 14. The sewage system includes an access line 16 through which the detector 10 is inserted and retrieved. The detector is held in place by a line 18 which is secured near the top of the access line by a securing system 20.

Figure 2:
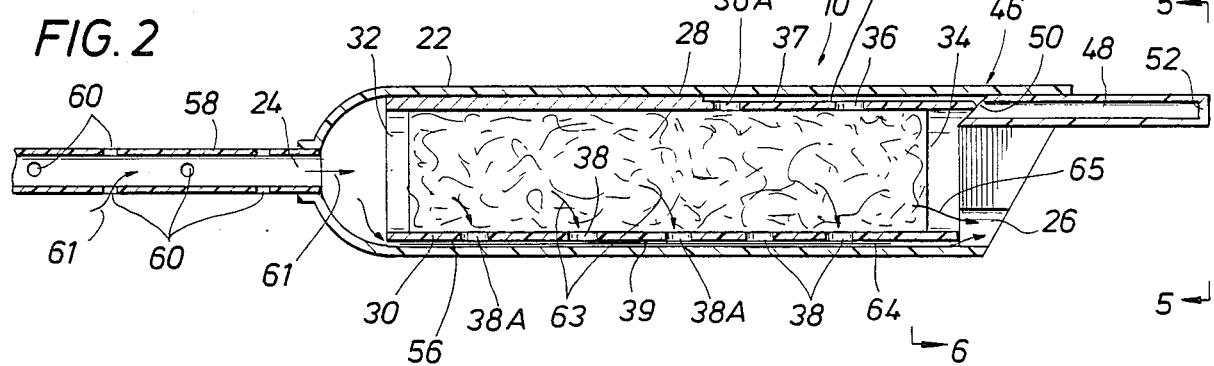
FIG. 2 is a cross-sectional elevation view of the detector portion of the present invention.
Figure 3:
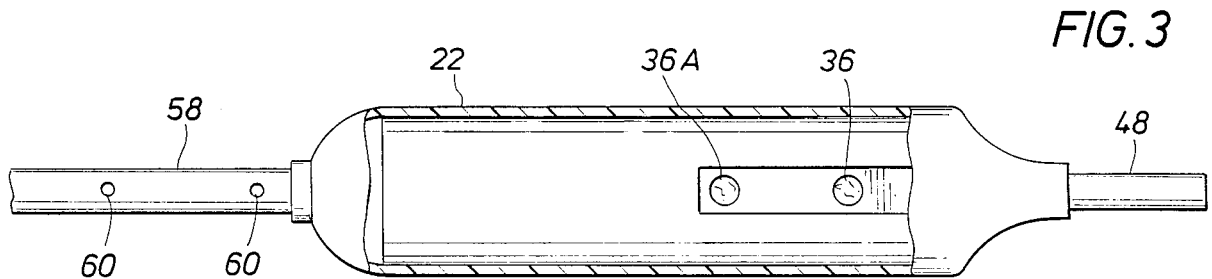
FIG. 3 is a top view of the detector partially in section.

Referring now to FIGS. 2-6, the detector 10 comprises a housing 22 having an inlet 24 and an outlet 26. An oleophilic material 28 is supported within the housing 22. As shown in FIG. 2, the oleophilic material is supported by an elongate member 30 which is open on both ends 32 and 34 and includes apertures 36A and 36 at the top 37 or along one side of the support member 30 and apertures 38A and 38 on the opposite or bottom side 39 of the support member 30.

Figure 6:
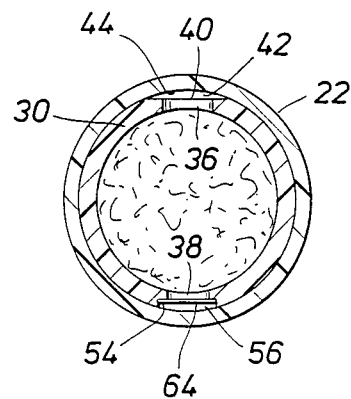
FIG. 6 is a cross-sectional view taken along line 6—6 of FIG. 2.

With particular reference to FIG. 6, the support member 30 includes a flat portion 40 along a portion of the top of the member 30 which defines a channel region 42 between the flat portion 40 or the top of the support member 30 and the interior surface 44 of the housing 22. The apertures 36A and 36 permit fluid communication between the interior of the support member 30 and the channel region 42. The channel extends from the first aperture 36A, along the length of the support member 30 toward the rear 46 of the housing 22. As defined, the channel region 42 terminates into a tube 48 which is open at one end 50 but sealed at its other 52.

Figure 5:
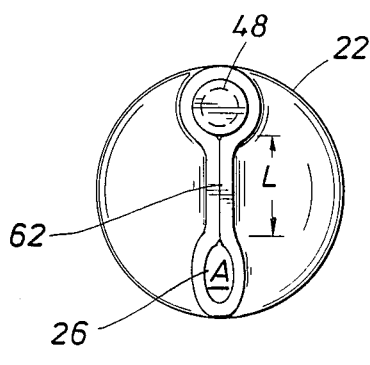
FIG. 5 is an end view taken along line 5—5 of FIG. 2.

With particular references to FIGS. 5 and 6, the bottom portion of the support member 30 includes apertures 38A and 38 which permit fluid communication with a flat portion 54 which extends along the entire length of the support member 10 thereby defining a channel region 56. The channel region 56 is defined by flat portion 54 of support member 30 and the interior surface of the housing 22. Since the flat portion 54 extends along the length of the support member 30, the channel region 56 also extends from front end 32 of the support member 30 to the rear end 46 of the housing 22 which is proximate the outlet 26.

As shown in FIG. 2, the housing 22 includes an inlet 24 to which an inlet member 58 is attached. The inlet member includes a plurality of apertures 60 along at least a portion of its length around its circumference. The detector is held in the position shown in FIG. 2 (with the collection tube 48 at the top) by molding or packaging the line 18 or inlet member 58 so that it includes a radius and thereby curves as shown in FIG. 1 in that region where the access line 16 intersects the main sewage line.

With reference to FIG. 5, a portion 62 of the rear of the housing is heat sealed or glued together around the tube 48 leaving the outlet 26. In this manner, the area "A" of the outlet 26 may be selected by controlling the length "L" of the sealed portion 62 so that a pressure differential is created for reasons discussed below.

Figure 4:
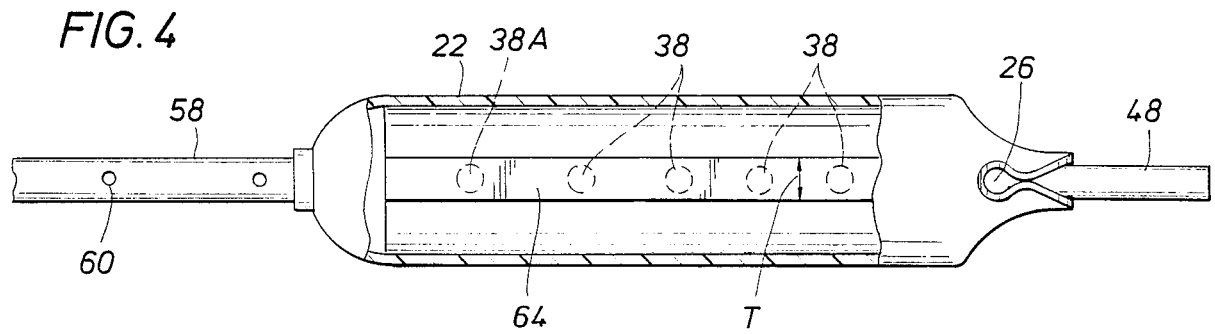
FIG. 4 is a bottom view of the detector partially in section.

With reference to FIGS. 4 and 6, the width "T" of the channel region 56 is selected to accommodate a strip of litmus paper 64 which is thereby situated within the flow path of the effluent passing through the channel region 56.

In the operation of the detector, the detector 10 is placed within the sewage system 12 so that the housing 22 floats on the surface of the effluent stream 66. In this manner, at least a portion of the effluent enters the inlet member through the apertures 60 (as shown by arrows 61) and passes into the housing 22 through the inlet 24. Most of the effluent continues into the support member 30 and passes through the oleophilic material 28. The oleophilic material attracts oil within the effluent stream and the oil migrates upwardly since it is lighter than the remaining portion of the effluent stream through apertures 36A and 36. The oil then enters the channel region 42 and flows down the channel region into the collection tube 48. The remaining portion of the effluent stream which passes through the oleophilic material either flows downwardly through the apertures 38A and 38 into the channel region 56 (as shown by arrows 63) or out the rear of the support member through the outlet 26 (as shown by arrow 65). Some of the effluent which enters the housing 22 through inlet 24 will enter the channel 56 below the front end 32 of the support member 30 rather than pass through the oleophilic material. The effluent stream which enters the channel region 56 either at the front of the support member 30 or through the apertures 38A and 38 contacts the litmus paper 64 which records acidity or pH and then exits through the outlet 26.

Preferably, the housing 22 is made of a polyvinylchloride clear plastic tubing as is the collection tube 48. Since they are clear, the oil in the collection tube and the pH measured by the litmus paper are easily observable. The support member 30 may be manufactured of plastic, metal or other material which is non-reactive to oil or acidic solutions. The oleophilic material may be made of polyurethane material as manufactured by such companies as Polyurethane Products of Addison, Ill., and Plastics Specialities of Austin, Tex. These materials are characterized occasionally as "sorbents." The litmus paper used may be any commercially available paper such as the type Color Phust ® manufactured by CCB Incorporated of Gibbstown, N.J. The litmus paper may include various levels of sensitivity and may measure the full range of pH desirable (i.e., acidic or alkaline).

Preferably, the cross-sectional area of the outlet 26 is smaller than the cross-sectional area of the inlet 24 to create a pressure differential and restrict the flow of the effluent stream passing through the support member. In this manner, the entrapment of oil contaminants within the oleophilic material is promoted. The cross-sectional area of the outlet 26 should not be more than 70 percent of the cross-sectional area of the inlet 24 to achieve optimum results.

Based on experimentation, it has been determined that for an effluent stream having one part oil to four parts water, there will be a visible collection of oil in the tube 48 within five minutes of immersion in the effluent stream. In these particular experiments, the oleophilic material used was Scot Foam ®, which is available through Scot Foam, a division of GFI of Eddystone, Pa. The housing 22 was approximately three inches long and ⅝ inches in diameter. The collection tube was about 1 and ½ inches long and had an inner diameter of about ⅛ inch. The channel region 42 was about 2 and ½ inches long and about ¼ inch wide. The channel region 56 was about 1 and ½ inches long and about ¼ inches wide. The diameter of the inlet 24 was about ⅛ inches and the outlet 26 was oblong after sealing the end of the housing and about 1/16 inches wide.

While the detector may be inserted in the sewage system and left there for an extended period of time, it may also be installed and left in place for only a few moments to obtain a current reading.

Figure 7:
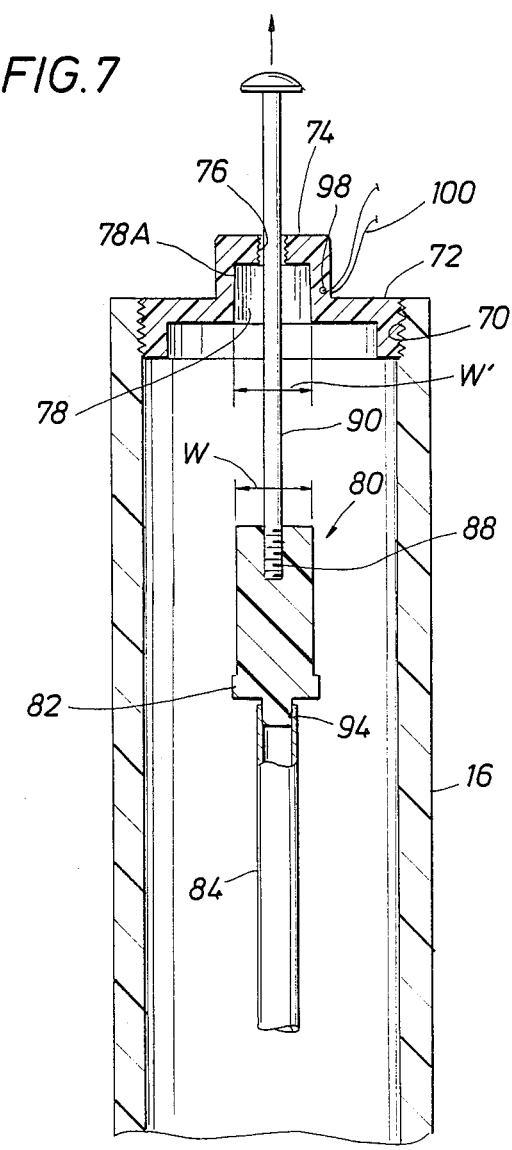
FIG. 7 is a cross-sectional elevation view of a portion of the securing system for attaching the detector to the access line.

Reference is now made to FIG. 7 for a discussion of the attachment of the detector 10 to the access line 16. In typical commercial establishments the access line 16 includes a threaded portion 70 adapted to receive a cap 72. Therefore, the present invention is intended to accommodate the use of existing access lines 16. The cap 72 includes a raised portion 74 to permit the use of a wrench or other tool to tighten the cap 72 to the access line 16 once threadably engaged. The raised portion 74 includes a threaded section 76, the purpose of which is discussed below. Within the raised portion 74 is a recessed portion or area 78. The recessed area 78 is adapted to receive a plug member 80. The plug member 80 includes a connector portion 82 which is attached to the lead line 18. The lead line 18 may be coupled to the inlet member 58 or the inlet member 58 and the lead line 18 may be the same. The plug also includes a threaded portion 88 to receive a key 90 whose operation is described below. The dimension W of the plug 80 is selected to fit in a snug manner within the dimension W' of the recessed area 78. Since the cap 72 and plug 80 would be made of polyvinylchloride (PVC) typically, the dimensions W and W' may be substantially the same. Alternatively, the wall 78A of the recessed portion may be tapered inwardly slightly as shown to provide a snug fit. A cover 92 is adapted to be inserted over the raised portion 74 of the cap 72 and attached by means of a bolt 96 or other threaded member to the threaded portion of the cap.

In the operation of this portion of the invention, the inlet member 58 or lead line 18, which is already attached to the detector 10 at one end, is attached at its other end to the connector 82. The connection may be made by a nipple 94 which is inserted into the inlet member or lead line. The detector is then inserted down the access line 16 into the main sewage line taking into account the radius or bend of the lead line 18 or the inlet member 58 so that the detector is oriented properly as shown in FIG. 2 with the collection tube at the top. The key 90 is then passed through the threaded portion 76 of the Cap 72 and threadably engaged with the threaded portion 88 in the plug 80. Since the threaded portion 76 has a larger diameter than the outer diameter of the key 90, the key 90 will slide easily within threaded portion 76. The cap 72 is then screwed into the threaded portion of the access line 16. And since the key 90 can slide within the threaded portion 76, the cap 72 may be screwed down onto the access line without rotating the key 90 and thereby twisting the detector within the sewage system. The plug 80 is then pulled into the recessed area 78 by pulling up on the key 90, and the plug is thereby held in place by a friction connection. At that point, the key 90 may be easily unscrewed from the threaded portion 88 of the plug because of the friction fit of the plug 80 within the cap 72 The cover 92 is then placed over the cap 72 and a bolt 96 fastens the cover 92 to the cap 72. The bolt 96 also seals against the top of the cover 92 thereby prohibiting seepage of offensive sewage odors out of the access line.

To record if anyone tampers with the detector, the raised portion 74 of the cap includes an aperture 98 and a wire 100 is passed through the aperture 98 and a passageway 102 within the head of the bolt 96. A security lock or lead crimp 104 may then be inserted and crimped sealed. Such security locks are of a style Lead Seal ® manufactured by E. J. Bruks of Dallas, Tex. As a back up or alternative security measure to ensure that no one has tampered with the detector, an adhesive tape 108 may be stretched across the top of the access line and the cap. The tape would include a hole for the bolt 96 to pass through or one may be made easily by the installer. After the tape is placed, the cover 92 would be installed. The tape 108 as well as the lead crimp lock 104 may include written materials and other descriptors of the appropriate regulatory authority, the date of inspection, the type of detector, etc. Thus, if anyone tried to remove the cap the lead crimp 104 would be damaged which would indicate a tampering. Further, if anyone tried to remove the cover, the tape would reflect such.

Figure 8:
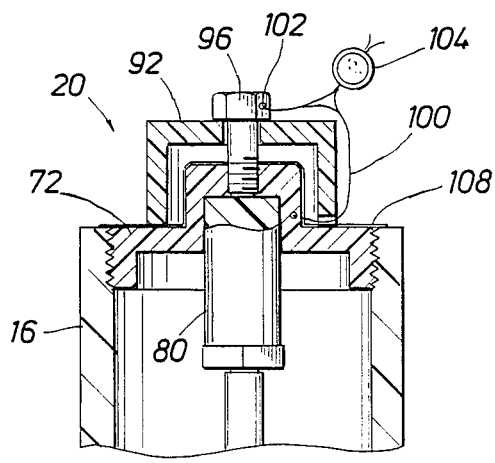
FIG. 8 is a cross-sectional elevation view of the securing system shown in a final position.
Figure 9:
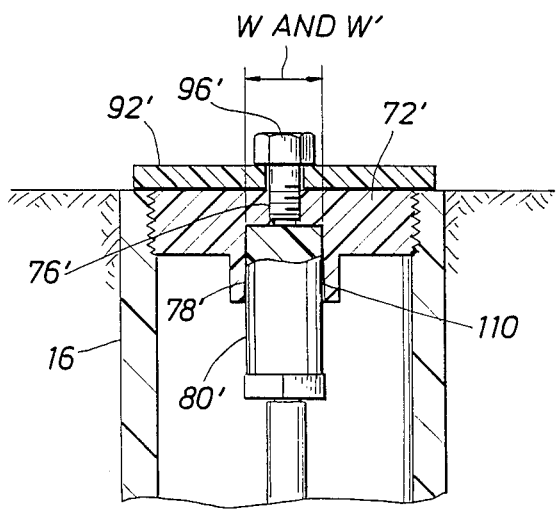
FIG. 9 is an alternate embodiment of the securing system shown in FIG. 8.

Referring now to FIG. 9 an alternate embodiment of the cap 72' and cover 92' is shown. The plug 80' is similar to that disclosed previously with respect to FIG. 7. The cap 72' is flat to permit vehicles to pass over or to provide a flush contour at the ground surface for whatever reason. The cap 72' includes a recess portion 78' defined by walls 110. Again, the dimension W' is selected so that it is substantially the same as the dimension of W of the plug or tapered to provide a snug fit as described above. The cap 72' includes a threaded portion 76' to receive a bolt 96' which is used to secure the over 92' to the top surface of the cap 72' once the plug 80' is installed. The operation of the alternate embodiment shown in FIG. 8 is identical to that discussed earlier with respect to FIG. 7. That is, the detector is installed in the access line 16 in the manner described above and a key 90 is then passed through the cap 72' and attached to the plug. The cap 72' is then screwed down flush with the ground surface and the key is pulled upwardly engaging the plug within the recessed area 78' of the cap 72'. The key 90 is then unscrewed, the cover 92' installed, and the bolt 96' inserted. To ensure that no one tampers with the detector, a tape may be passed across the top of the access line and the cap before the cover is installed as discussed earlier. The unit may be sealed with a wax or resin with the seal of the public agency impressed within the seal or resin thereby permitting the sealing of the system without the worry of vehicles destroying the verification system.

Obviously, the embodiment shown in FIG. 9 may be easily modified based on this disclosure to make it more flush with the ground surface. For example, the top of the access line 16 and the cap 72' may include a recessed area which would permit the cover 92' to be flush with the ground surface once installed. The region for the bolt head 96' within the cover 92' would then be countersunk so that the top of the bolt would be flush with the top of the cover 92' as well as the ground surface.

In removing the detector for inspection, the inspector would merely break the seals and disassemble the cap. That is, the bolt 96 would be unscrewed and the cover 92 removed. At that time, the key 90 would be inserted through the threaded portion 76 and screwed into the threaded portion 88 of the plug 80. The key would then be pushed downwardly thereby dislodging the plug from the cap. Since the key includes a head, it may be released and would still hang from the top of the cap 72 holding the plug 80 and detector 10. The cap 72 would be unscrewed from the access line 16 and the entire assembly removed. Since the detector is attached by means of the inlet line or lead line to the plug, the entire assembly is easily removed. A quick visual inspection of the collection tube 48 as well as the litmus paper 64 will give the inspector an indication of whether or not oil has been dispersed in the effluent stream and the maximum or minimum pH of the effluent stream since the last inspection. If the inspector wishes to obtain an immediate sampling, a new indicator may be installed and sampling obtained over a short period of time. Since the detectors are disposable, there is no need to disassemble each detector for cleaning before it is used.

The present invention has been described in terms of particular embodiments. Obviously, modifications and alterations to these embodiments will be apparent to those skilled in the art in view of this disclosure. It is, therefore, intended that all such equivalent modifications and variations fall within the spirit and scope of the present invention as claimed.

What is claimed is:

1. An apparatus for continuously detecting the presence of oil and other contaminants in an effluent stream passing through a pipeline comprising:
    a housing having an inlet and an outlet;
    oleophilic means supported within said housing so that at least a portion of the effluent stream enters said housing through said inlet and passes through said oleophilic means;
    means for supporting said oleophilic means within said housing; and
    means for collecting and displaying the presence of oil absorbed by said oleophilic means, said collecting and displaying means comprising a tube having one end attached within said housing and having the other end substantially sealed.

2. The apparatus according to claim 1 wherein said support means comprises a hollow elongate member including a substantially flat portion having at least one aperture through said flat portion forming a channel region above said oleophilic means between the interior surface of said housing and said flat portion so that oil absorbed by said oleophilic means is permitted to rise into said channel region.

3. The apparatus according to claim 2 wherein said elongate member includes at least one aperture below said oleophilic means forming a second channel region between the outer surface of said elongate member and the interior surface of said housing so that at least a portion of the effluent stream passing through said housing exits through said second channel region.

4. The apparatus of claim 1 wherein said apparatus further comprises an elongate inlet member attached at one end to said inlet of said housing and having a plurality of apertures along at least a portion of said inlet member to permit at least a portion of the effluent stream to enter said inlet member and thereby enter said housing.

5. The apparatus of claim 1 wherein the cross-sectional area of said outlet being no more than 70% of the cross-sectional area of said inlet forms a pressure differential promoting the movement of the oil towards said collecting and displaying means.

6. The apparatus of claim 3 wherein said apparatus further comprises means for detecting the pH of the effluent stream in said second channel region.

7. An apparatus for continuously detecting the presence of oil and other contaminants in an effluent stream passing through a pipeline comprising:
   a housing having an inlet and an outlet;
   oleophilic means supported within said housing so that at least a portion of said effluent stream enters said housing through said inlet and passes through said oleophilic means;
   means for supporting said oleophilic means wherein said support means forms a channel region above said oleophilic means so that oil absorbed by said oleophilic means is permitted to rise into said channel region; and
   means for collecting and displaying the presence of oil contaminants entering said channel region.

8. The apparatus of claim 7 wherein said support means and said housing forms a second channel region below said oleophilic means so that at least a portion of the effluent stream passing through said housing exits through said second channel region.

9. The apparatus of claim 8 wherein said apparatus further comprises means for detecting the pH of the effluent stream in said second channel region.

10. The apparatus according to claim 9 wherein said detecting means for determining the pH of the effluent stream comprises litmus paper.

11. The apparatus of claim 7 wherein said apparatus further comprises an elongate inlet member attached at one end to said inlet of said housing and having a plurality of apertures along at least a portion of said inlet member to permit at least a portion of the effluent stream to enter said inlet member and thereby enter said housing.

12. The apparatus of claim 7 wherein the cross-sectional area of said outlet being no more than 70% of the cross-sectional area of said inlet forms a pressure differential promoting the movement of the oil towards said collecting and displaying means.

13. An apparatus for continuously detecting the presence of oil and other contaminants in an effluent stream passing through a pipeline comprising:
   a housing having an inlet and an outlet;
   an elongate inlet member attached at one end to said inlet of said housing and having a plurality of apertures along at least a portion of said inlet member to permit at least a portion of the effluent stream to enter said housing through said inlet member;
   oleophilic means supported within said housing wherin at least a portion of said effluent stream entering said housing through said inlet member passes through said oleophilic means;
   a hollow elongate member for supporting said oleophilic means including a substantially flat portion having at least one aperture through said flat portion forming a first channel region above said oleophilic means between the interior surface of said housing and said flat portion so that oil absorbed by said oleophilic means rises into said first channel region, said elongate member having at least one aperture below said oleophilic means forming a second channel region between the outer surface of said elongate member and the interior surface of said housing so that at least a portion of the effluent stream passing through said housing exits through said second channel region to said outlet;
   means for collecting and displaying oil in said first channel region; and
   means for detecting the pH of the effluent stream in said second channel region.

14. The apparatus according to claim 13 wherein said apparatus further comprises:
   means for securing said inlet member to the pipeline, said securing means including:
      a cap adapted to engage the pipeline and having a recessed portion of a predetermined minimum width;
      a plug having an exterior width substantially the same as said predetermined minimum width of said cap and a connector adapted to attach to said inlet member;
      a cover adapted to contact said cap; and
      means for verifying the movement of the cap relative to the cover.

15. The apparatus according to claim 13 wherein said recessed portion of said cap includes tapered walls.

16. An apparatus for securing a lead line of a detector within an access line of a pipeline comprising:
   a cap adapted to engage the access line and having a recessed portion of a predetermined interior width;
   a plug having an exterior width substantially the same as said predetermined interior width of said recessed portion and having a connector adapted to attach to said lead line;
   a cover adapted to contact said cap; and
   means for verifying the movement of the cap relative to the access line.

17. An apparatus for securing a detector having a lead line to an access line of a pipeline comprising:
   a cap adapted to engage the access line and having a recessed portion of a predetermined interior width and a threaded portion passing through said cap into said recessed portion;
   a plug having (i) an exterior width substantially the same as said predetermined interior width of said recessed portion, (ii) a connector adapted to engage the lead line of said detector, and (iii) a threaded portion of smaller diameter than the threaded portion of said cap and coaxially aligned with said threaded portion of said cap when said plug is inserted in said recessed portion;
   key means having a threaded portion to threadably engage said plug to permit the insertion of said plug within said recessed portion of said cap;
   a cover having an aperture coaxially aligned with said threaded portions of said cap and said plug and adapted to contact said cap; and
   means for verifying the movement of the cap relative to the access line.

* * * * *

UNITED STATES PATENT AND TRADEMARK OFFICE
CERTIFICATE OF CORRECTION

PATENT NO.  : 4,863,692

DATED       : September 5, 1989

INVENTOR(S) : Arnold D. Plumb

It is certified that error appears in the above-identified patent and that said Letters Patent is hereby corrected as shown below:

Column 4, line 3, "CCB" should read -- MCB --.

Column 5, line 8, "Cap" should read -- cap --.

Column 5, line 22, "72" should read -- 72. --.

Column 5, line 58, "over" should read -- cover --.

Column 8, line 2, "wherin" should read -- wherein --.

Signed and Sealed this

Fourteenth Day of August, 1990

Attest:

HARRY F. MANBECK, JR.

*Attesting Officer*     *Commissioner of Patents and Trademarks*